000
United States Patent [19]

Nishizawa, deceased et al.

[11] Patent Number: 4,552,975

[45] Date of Patent: Nov. 12, 1985

[54] MANUFACTURING PROCESS FOR N-CARBOBENZYLOXY-L-GLUTAMIC ACID-α-CHOLINESTER SALT

[75] Inventors: Yoshito Nishizawa, deceased, late of Tokushima, Japan, by Hisako Nishizawa, heir; Matao Kanaoka, Toyama, Japan

[73] Assignee: Moringa Milk Industry, Co., Ltd., Tokyo, Japan

[21] Appl. No.: 640,190

[22] Filed: Aug. 13, 1984

[30] Foreign Application Priority Data

Aug. 13, 1983 [JP] Japan ................................. 58-147289

[51] Int. Cl.$^4$ ......................................... C07C 125/065
[52] U.S. Cl. ..................................................... 560/163
[58] Field of Search ......................................... 560/163

[56] References Cited

FOREIGN PATENT DOCUMENTS 66856 12/1982 European Pat. Off. .
43-213 1/1968 Japan ..................................... 560/163

Primary Examiner—Michael L. Shippen
Attorney, Agent, or Firm—Jordan and Hamburg

[57] ABSTRACT

The invention relates to manufacturing process for a halide or an organic sulfonate of N-carbobenzyl-L-glutamic acid-α-cholinester in high purification, which is useful as e.g. hypotensive drug. According to the prior art, undesired γ-form byproduct is inevitably formed to be mingled with said α-form objective compound of which separation is difficult. It has been found that when using N-carbobenzyloxy-γ-tert. butyl-L-glutamic acid-dicyclohexyl-ammonium salt readily available in high purification as starting material, reacting N, N-dimethyl-aminoethylchloride therewith to form N-carbobenzyloxy-γ-tert. butyl-L-glutamic acid-α-dimethylaminoethyl ester which is quaternerized to form N-carbobenzyloxy-γ-tert. butyl-L-glutamic acid-α-cholinester salt, which is subjected to mild salt treatment, the objective compound can be obtained in high purification.

3 Claims, No Drawings

MANUFACTURING PROCESS FOR N-CARBOBENZYLOXY-L-GLUTAMIC ACID-α-CHOLINESTER SALT

FIELD OF THE INVENTION

The invention relates to a process for manufacturing N-carbobenzyloxy-L-glutamic acid-α-cholinester salt, and more particularly N-carbobenzyloxy-L-glutamic acid -α-cholinester salt involving no isomer thereof, namely N-carbobenzyloxy-L-glutamic acid-γ-cholinester salt.

BACKGROUND OF THE INVENTION

N-carbobenzyloxy-L-glutamic acid-α-cholinester chloride has been in public knowledge to be useful as hypotensive drug, lipotropic drug and infantile paralysis therapeutical agent ("Jap. Chem. Soc., 72, No. 3. 46–47 (1951); Vitamin; 7, No. 4 (Separate Volume, 428–467 (1954)). According to said technical magazines N-carbobenzyloxy-L-glutamic acid-α-cholinester halide, which may be called a sort of the salt in the broad meaning, is inevitably obtained in the form of mixture with γ-form in the known method. It is very difficult, however, to isolate N-carbobenzyloxy-L-glutamic acid-α-cholinester salt from the mixture to be purified, since said α- and γ-forms are of extremely similar physicochemical properties due to their similar chemical structures as shown below;

N-Carbobenzyloxy-L-Glutamic Acid-α-Cholinester Salt (α-form)

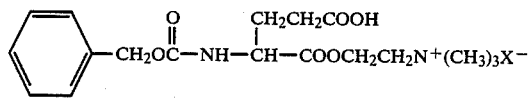

N—Carbobenzyloxy-L-Glutamic Acid-γ-Cholinester Salt (γ-Form)

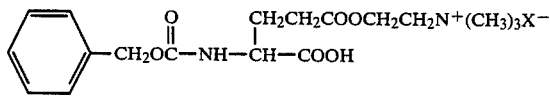

Said X means a halogen or an organic sulfonate.

SUMMARY OF THE INVENTION

The object of the invention is, thus, to provide a process for industrially manufacturing N-carbobenzyloxy-L-glutamic acid-α-cholinester salt mingled with no N-carbobenzyloxy-L-glutamic acid-γ-cholinester salt.

The inventors have tried to provide such process to find out that N-carbobenzyloxy-γ-tert.butyl-L-glutamic acid-dicyclohexyl-ammonium salt, which may be a starting material for synthesizing said objective compound, can be readily crystalyzed and purified by means of solvent to obtained in high purification in comparison with similar starting materials such as N-carbobenzyloxy-γ-tert.butyl-glutamic acid. The invention is based on such finding.

Said object can be attained according to the invention by proceeding with a process comprising three steps of (a) that N-carbobenzyloxy-γ-tert.butyl-L-glutamic acid-dicyclohexyl-ammonium salt as starting material is reacted with dimethylaminoethylchloride to form N-carbobenzyloxy-γ-tert.butyl-L-glutamic acid-α-dimethylaminoethyl ester, (b) that obtained N-carbobenzyloxy-γ-tert.butyl-L-glutamic acid-α-dimethylaminoethyl ester is reacted with a quaternerizing agent for the dimethylamino-group to form N-carbobenzyloxy-γ-tert.butyl-L-glutamic acid-α-cholinester salt, and (c) that obtained N-carbobenzyloxy-γ-tert.butyl-L-glutamic acid-α-cholinester salt is subjected to mild acid treatment for selectively removing of the tert.butyl-group at the γ-position to obtain the final product, N-carbobenzyloxy-L-glutamic acid-α-cholinester salt. Said objective compound is used as hypotensive drug, lipotropic drug and infantile paralysis therapeutical preparation.

DETAILED EXPLANATION OF PREFERRED EMBODIMENT

The objective compound of the invention, N-carbobenzyloxy-L-glutamic acid-α-cholinester salt is manufactured from the starting material, N-carbobenzyloxy-γ-tert.butyl-L-glutamic acid-dicyclohexyl ammonium salt through the three steps as referred to above.

The reaction steps may be shown by formulae as follows;

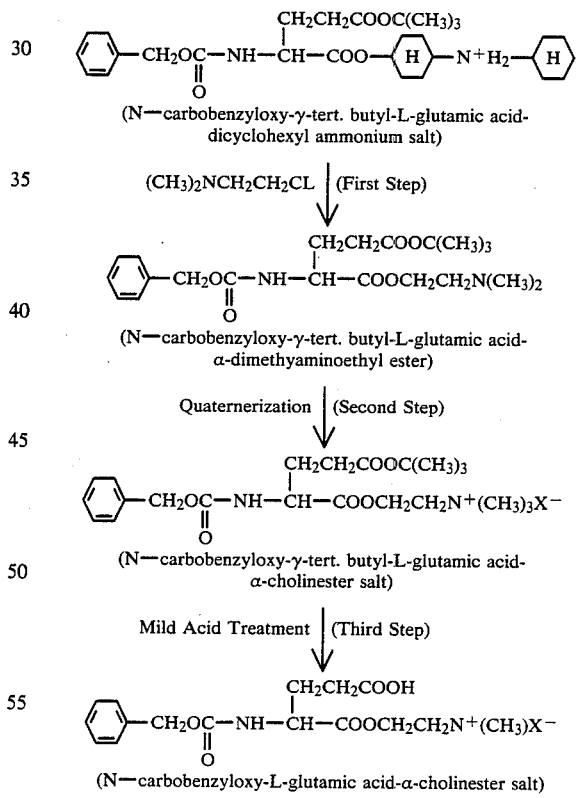

The starting material in the process of the invention, N-carbobenzyloxy-γ-tert.butyl-L-glutamic acid-dicyclohexyl-ammonium salt may be manufactured according to the process described in Ann. Chem; 655, 195–210 (1965). This is so readily crystalized and purified by means of solvent as to obtain in high purification in comparison with N-carbobenzyloxy-γ-tert.butyl-L-glutamic acid. Said starting material should not involve N-carbobenzyloxy-α-tert.butyl-L-glutamic acid-dicyclohexyl-ammonium salt, the isomer of said starting material, since there is caused no rearrangement of the respective atomic groups at γ- and α-positions in L-glutamic acid in the reactions of the second and third steps of the process according to the invention.

In the first step of the invention, N-carbobenzyly-γ-tert.butyl-L-glutamic acid-dicyclohexyl ammonium salt is suspended in an organic solvent, to which a solution of dimethylaminoethylchloride is added. As solution for suspending N-carbobenzyloxy-γ-tert.butyl-L-glutamic acid-dicyclohexyl-ammonium salt, ethyl acetate, acetonitrile, chloroform, methylene chloride and other organic solvent as well as mixture thereof are preferably used. As solvent for dissolving dimethylaminoethylchloride, an aromatic hydrocarbon solvent such as benzene, toluene and xylene, an ether solvent such as diethyl ether, tetrahydrofuran and dioxane, as well as a mixture thereof are preferably used.

The ratio of N-carbobenzyloxy-γ-tert.butyl-L-glutamic acid-dicyclohexyl ammonium salt to dimethylamino-ethylchloride to be added is preferably more than the stoichiometrical volume of the latter to the former. Said first step reaction is preferably carried out at a raised temperature.

In said first step, N-carbobenzyloxy-γ-tert.butyl-L-glutamic acid-dicyclohexyl ammonium salt suspended in the organic solvent is reacted with dimethyl-aminoethylchloride in the solution to form N-carbobenzyloxi-γ-tert.butyl-L-glutamic acid-dimethylaminoethyl ester (Intemediate I) and dicyclohexyl-ammonium chloride to be precipitated.

In the second step of the invention, said Intermediate I is dissolved in an organic solvent, to which a solution of a quaternarizing agent for the dimethylamino-group in the same solvent is added for the reaction.

As the solvent therefor, any of the solvents referred to above as to the first step may be used. As the quaternerizing agent, a methyl halide such as methyl chloride, methyl bromide and methyl iodide, an organic methyl sulfonate such as methyl parasulfonate are preferably used. Said quatererizing agent is added preferably in the amount more than the stoichiometric volume relative to the Intermediate I. Said reaction goes through at a room temperature, but may be carried out at a raised temperature in order to accelerate the reaction speed.

In said second step, the dimethylamino-group of said Intermediate I is added with methyl to form choline which is added with a halogen or an organic sulfonic acid to form ammonium ion. Thereby N-carbobenzyloxy-γ-tert.butyl-L-glutamic acid-α-cholinester-halide or -organic sulfonate (Intermediate II).

In the third step of the invention, the obtained Intermediate II is added with solution of an acid in an organic solvent. The acid to be preferably used for such mild treatment, can be any selected from a class consisting of trifluoroacetic acid, hydrogen chloride, acetic acid, formic acid, propionic acid, paratoluenesulfonic acid and Lewis acids. Such acid is added in the form of solution in an organic solvent to be reacted with the Intermediate II. The reaction goes through at a room temperature but may be carried out at a raised temperature.

In said third step reaction, only the tert.butyl-group of said Intermediate II is decomposedly removed to form the objective compound, N-carbobenzyloxy-L-glutamic acid-α-cholinester-halide or -organic sulfonate.

Since no transition of atomic groups bonded at γ- and α-positions is caused through said reactions of the invention, when using N-carbobenzyloxy-γ-tert.butyl-L-glutamic acid-dicyclohexyl ammonium of high purity only as starting material, it is possible to obtain N-carbobenzyloxy-L-glutamic acid also of high purity as objective compound. It is to be noted that such highly purified starting material is readily available by reasons as referred to above.

Step Example 1 (Starting Material→Intermediate I)

To 1.88 g N-carbobenzyloxy-γ-tert.butyl-L-glutamic acid-dicyclohexyl ammonium salt, 24 ml ethyl acetate and 3.3 ml solution of dimethylaminoethylchloride in the amount of 0.78 g, stoichiometrically corresponds to two times the molar volume, in benzene were added to be subjected to reflux in oil bath at 90° C. for 16 hrs. After cooling down to a room temperature, precipitated dicyclohexyl ammonium chloride was filtered off and ethyl acetate phase in the filtrate was washed with diluted hydrochloride to remove excessive dimethylaminoethylchloride contained therein. The filtrate was further washed with 10% aqueous solution of hydrogen sodium bicarbonate so as to remove unreacted starting meterial, N-carbobenzyloxy-γ-tert.butyl-L-glutamic acid-dicyclohexyl-ammonium salt and then with saturated brine to be neutral, which was then treated with sulfuric sodium anhydride for dehydration and subjected to reduced pressure distillation so as to distill off ethyl acetate and obtain Intermediate I, N-carbobenzyloxy-γ-tert.butyl-L-glutamic acid-dimethylamino-ethyl ester in the amount of 1.43 g (yield; 96.6% by weight).

After development of obtained N-carbobenzyloxy-γ-tert.butyl-L-glutamic acid-α-dimethylaminoethyl ester on the thin layer sheet of silica gel with fluorescent agent manufactured by Merck & Co., Inc. (Art. 5715, KIESELGEL 60F-254) which shall be abridged as "Art. 5715" hereafter, with using chloroform methanol acetic acid (95:5:3 by volume) as development solvent, the sample was colored with ninhydrin reagent after ultraviolet radiation (254 nm) or treatment with Dragendorf reagent, hydrobromic acid, which shall be called TLC-A method hereafter. The same sample was developed on said Art. 5715 with using n-buthanol/acetic acid/water (4:1:2 by volume) as development solvent and then colored according to the same means as in said TLC-A method, which shall be called TLC-B method hereafter. Said sample showed single spot according to either of said TLC-A and TLC-B methods.

Said sample was examined by means of Varian EM 390 NMR Spectrometer to show following NMR spectrum;

NMR(CDCl$_3$)δ: 1.38(9H, s, C(CH$_3$)$_3$, 1.93(2H, m, —CH$_2$—), 2.25(6H, s, —N(CH$_3$)$_2$), 2.32(2H, m, —CH$_2$CO), 2.55(2H, t, —CH$_2$N<), 4.21(2H, t, —OCH$_2$), 4.30(1H, m, >CHCO), 5.08(2H, s, C$_6$H$_5$—CH$_2$), 5.53(1H, br, —NH—), 7.35(5H, s, C$_6$H$_5$—).

From the above it was confirmed that the obtained Intermediate I had the structure well consistent with that of N-carbobenzyloxy-γ-tert.butyl-L-glutamic acid-α-dimethylaminoethyl ester.

Step Example 2 (Starting Material→Intermediate I)

To 1.20 g N-carbobenzyloxy-γ-tert.butyl-L-glutamic acid-dicyclohexyl ammonium salt, 20 ml methylene chloride and 2.1 ml solution of dimethylamioethyl-chloride in the amount of 0.5 g, which stoichiometrically corresponds to two times molar volume, in toluene were added to be subjected to reflux in oil bath at 50° C.

for 35 hrs. After cooling down to the room temperature, the reaction mixture was similarly treated as in Step Example 1 to obtain N-carbobenzyloxy-γ-tert.butyl-L-glutamic acid-α-dimethylaminoethyl ester in the amount of 842 mg (yield; 89.1%).

The sample thereof was subjected to the thin layer chromatography according to the TLC-A and TLC-B methods to result in the same Rf value and color of the spots as in Step Example 1 and single spot in the mixture development. NMR spectrum determined according to the spectrometer used in Step Example 1 was also consistent with that of N-carbobenzyloxy-γ-tert.butyl-L-glutamic acid-α-dimethylaminoethyl ester.

Step Example 3 (Starting Material→Intermediate I)

To 1.10 g N-carbobenzyloxy-γ-tert.butyl-L-glutamic acid-dicyclohexyl ammonium salt, 1.8 ml chloroform and 1.9 ml solution of dimethylaminoethylchloride in the amount of 0.46 g, which stoichiometrically corresponds to two times molar volume, in dioxane were added to be subjected to reflux in oil bath at 70° C. for 30 hrs. After cooling down to a room temperature, said reaction mixture was similarly treated as in Step Example 1 to obtain N-carbobenzyloxy-γ-tert.butyl-L-glutamic acid-α-dimethylaminoethyl ester in the amount of 766 mg (yield; 88.4%).

The sample thereof was subjected to the thin layer chromatography according to the TLC-A and TLC-B methods to result in the same Rf value and color of the spots as in Step Example 1 and single spot in the mixture development. NMR spectrum was also just same with that given in Step Example 1.

Step Example 4 (Intermediate I→Intermediate II)

To 1.23 g N-carbobenzyloxy-γ-tert.butyl-L-glutamic acid-α-dimethylaminoethyl ester, 1.5 ml ethyl acetate and 7 ml solution of 1.5 g methyl chloride in benzene were added to stand still at a room temperature for 7 days and then to be subjected to the reduced pressure distillation to distill off the solvent and obtain the Intermediate II, N-carbobenzyloxy-γ-tert.butyl-L-glutamic acid-α-cholinester chloride in the amount of 1.38 g (yield; 99.7%).

The sample thereof resulted in single spot according to TLC-A and TLC-B methods. NMR spectrum thereof determined according to the spectrometer used in Step Example 1 are as follows.

NMR(CDCl$_3$)δ: 1.37(9H, s, c(CH$_3$)$_3$), 2.10(2H, m, —CH$_2$—), 2.27(2H, m, —CH$_2$CO), 3.32(9H, s, —N$^+$(CH$_3$)$_3$), 3.97(2H, m,

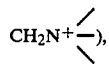

4.33(1H, m, >CHCO), 4.53(2H, m, —OCH$_2$—), 5.05(2H, s, C$_6$H$_5$—CH$_2$), 6.87(1H, br, —NH—), 7.35(5H, s, C$_6$H$_5$—).

From the above, it can be confirmed that the obtained Intermediate II has the structure well consistent with that of N-carbobenzyloxy-γ-tert.butyl-L-glutamic acid-α-cholinester chloride.

Step Example 5 (Intermediate I→Intermediate II)

To 1.65 g N-carbobenzyloxy-γ-tert.butyl-L-glutamic acid-α-dimethylaminoethyl ester, 2 ml ethyl acetate and 3.2 ml solution of 1.38 g methyl bromide in benzene were added to stand still at a room temperature one night and then to be subjected to reduced pressure distillation to remove the solvent and obtain the Intermediate II, N-carbobenzyloxy-γ-tert.butyl-L-glutmic acid-α-cholinester bromide in the amount of 2.03 g (yield; 99.8%).

The sample thereof resulted in single spot according to the TLC-A and TLC-B methods. NMR spectrum thereof determined according to the spectrometer used in Step Example 1 was also consistent with that given in Step Example 4.

Step Example 6 (Intermediate I→Intermediate II)

To 866 mg N-carbobenzyloxy-γ-tert.butyl-L-glutamic acid-α-dimethylaminoethyl ester, 1 ml ethyl acetate and 0.5 ml methyl iodide were added to stand still at a room temperature one night. The reaction mixture was then cooled in ice bath so as to get precipitated crystal phase by filtering, which was washed with a small amount of n-hexane and dried under vacuum to obtain the Intermediate II, N-carbobenzyloxy-γ-tert.butyl-L-glutamic acid-α-cholinester iodide in the amount of 1.13 g (yield; 96.8%). Melting point was 74°–79° C.

The sample thereof resulted in the single spot according to TLC-A and TLC-B methods. Ultimate Analysis C$_{22}$H$_{35}$O$_6$N$_2$I; Calculation Values C=48.01%, H=6.41%, N=5.09%; Determined Values C=48.00%, H=6.49%, N=5.04%, which are well consistent with those of N-carbobenzyloxy-γ-tert.butyl-α-cholinester iodide. NMR spectrum was also consistent with the spectrum thereof.

Step Example 7 (Intermediate I→Intermediate II)

To 720 mg N-carbobenzyloxy-γ-tert.butyl-L-glutamic acid-α-dimethyl-aminoethyl ester, 1 ml ethyl acetate and 0.65 g methyl paratoluenesulfonate to stand still at a room temperature one night and to be subjected to reduced pressure distillation to distill off ethyl acetate. The residue was washed with ether and cooled in ice bath so as to get precipitated crystal phase by filtering, which was further washed with ether and dried under vacuum to obtain the Intermediate II, N-carbobenzyloxy-γ-tert.butyl-L-glutamic acid-α-cholinester paratoluenesulfonate in the amount of 881 mg (yield; 83.4%). Melting point is 102°–105° C.

The sample thereof resulted in single spot according to the TLC-A and TLC-B methods. Ultimate Analysis C$_{29}$H$_{42}$O$_9$N$_2$S; Calculation Values C=58.57%, H=7.12%, N=4.71%; Determined Values =58.72%, H=6.94%, N=4.79%, which are well consistent with those of N-carbobenzyloxy-γ-tert.butyl-L-glutamic acid-α-cholinester paratoluenesulfonate. NMR spectrum thereof determined according to the spectrometer used in Step Example 1 was also consistent with that given in Step Example 4.

Step Example 8 (Intermediate II→Objective Compound)

To 130 mg N-carbobenzyloxy-γ-tert.butyl-L-glutamic acid-α-cholinester chloride, 0.5 ml trifluoroacetic acid/methylene chloride (1:1 by volume) was added with cooling in ice bath. After stirring in ice bath for 30 mins. and then at the room temperature for 3 hrs., the reaction mixture was subjected to the reduced pressure distillation to distill off the solvent. The residue was washed with ether to remove excessive trifluoroacetic acid, and dried under vacuum to obtain the objective compound, N-carbobenzyloxy-L-glutamic acid-α-cholinester chloride in the amount of 112 mg (yield; 98.1%).

The sample thereof resulted in single spot according to the TLC-B method to show the obtained objective compound consisting only of α-form. NMR spectrum determined according to the spectrometer used in Step Example 1 was as follows.

NMR (CDCl$_3$+(CD$_3$)$_2$SO)δ: 2.02(2H, m, —CH$_2$—), 2.43(2H, m, —CH$_2$CO), 3.18(9H, s, —N+(CH$_3$)$_3$), 3.77(2H, m,

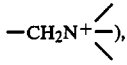

4.37(1H, m, >CHCO), 4.50(2H, m, —OCH$_2$—), 5.03(2H, s, C$_6$H$_5$—CH$_2$), 7.33(5H, s, C$_6$H$_5$—).

From the above, it can be confirmed that the obtained objective compound has the structure well consistent with that of N-carbobenzyloxy-L-glutamic acid-α-cholinester chloride.

Step Example 9 (Intermediate II→Objective Compound)

To 315 mg N-carbobenzyloxy-γ-tert.butyl-L-glutamic acid-α-cholinester bromide, 1.2 ml trifluoroacetic acid/methylene chloride (1:1 by volume) was added with cooling in ice bath. After stirring in the ice bath for 30 mins. and then at the room temperature for 3 hrs., the reaction mixture was treated as in Step Example 8 to obtain the objective compound, N-carbobenzyloxy-L-glutamic acid-α-cholinester bromide in the amount of 271 mg (yield; 96.8%).

Step Example 10 (Intermediate II Objective Compound)

To 100 mg N-carbobenzyloxy-γ-tert.butyl-L-glutamic acid-α-cholinester bromide, 1 ml hydrogen chloride/methylene chloride (0.1% by weight) with cooling in ice bath. After stirring in ice bath for 30 mins., and at the room temperature for 5 hrs., the reaction mixture was treated as in Step Example 8 to obtain the objective compound, N-carbobenzyloxy-L-glutamic acid-α-choline-ester bromide in the amount of 74 mg (yield; 83.5%).

The sample thereof resulted in single spot according to TLC-B method to show the obtained objective compound consisting only of α-form. NMR spectrum thereof also was well consistent with that of said α-form.

Step Example 11 (Intermediate II→Objective Compound)

To 130 mg N-carbobenzyloxy-γ-tert.butyl-L-glutamic acid-α-cholinester bromide, 0.5 ml mixture of 5N hydrogen chloride and ethyl acetate was added with cooling in ice bath. After stirring in ice bath for 60 mins. the reaction mixture was treated as in Step Example 8 to obtain the objective compound, N-carbobenzyloxy-L-glutamic acid-α-cholinester bromide in the amount of 110 mg (yield; 95.2%).

The sample thereof resulted in single spot according to the TLC-B method to show the otained objective compound consisting only of the α-form. NMR spectrum determined according to the spectrometer used in Step Example 1 was well consistent with that of the α-form.

Step Example 12 (Intermediate II→Objective Compound)

To 125 mg N-carbobenzyloxy-γ-tert.butyl-L-glutamic acid-α-cholinester chloride, 0.4 ml trifluoroacetic acid/chloroform (1:1 by volume) was added with cooling in ice bath. After stirring in ice bath for 30 mins. and at the room temperature for 3 hrs., the reaction mixture was treated as in Step Example 8 to obtain the objective compound, N-carbobenzyloxy-L-glutmic acid-α-cholinester chloride in the amount of 100 mg (yield; 91.1%).

The sample thereof resulted in single spot according to the TLC-B method to show the obtained objective compound consisting only of the α-form. NMR spectrum thereof determined aceording to the spectrometer used in Step Example 1 was well consistent with that of the α-form.

Step Example 13 (Intermediate→Objective Compound)

To 114 mg N-carbobenzyloxy-γ-tert.butyl-L-glutamic acid-α-cholinester chloride, with stirring, 0.4 ml 5N hydrogen chloride/ethyl acetate was added. The reaction mixture was treated as in Step Example 8, after stirring in ice bath for 60 mins. to obtain the objective compound, N-carbobenzyloxy-L-glutamic acid-α-cholinester chloride in the amount of 94 mg (yield; 93.9%).

The sample thereof resulted in single spot according to the TLC-B method to show the obtained objective compound consisting only of the α-form. NMR spectrum thereof determined according to the spectrometer used in Step Example 1 was well consistent with that of the α-form.

Step Example 14 (Intermediate II→Objective Compound)

To 150 mg N-carbobenzyloxy-γ-tert.butyl-L-glutamic acid-α-cholinester bromide, with cooling in ice bath, 0.5 ml 4N hydrogen chloride/dioxane was added. The reaction mixture was treated as in Step Example 8, after stirring in the ice bath for 90 mins., to obtain the objective compound, N-carbobenzyloxy-L-glutamic acid-α-cholinester iodide in the amount of 121 mg (yield; 89.8%).

The sample thereof resulted in single spot according to the TLC-B method to show the obtained objective compound consisting only of the α-form. NMR spectrum thereof determined according to the spectrometer used in Step Example 1 was well consistant with that of the α-form.

Step Example 15 (Intermediate II→Objective Compound)

To 124 mg N-carbobenzyloxy-γ-tert.butyl-L-glutamic acid-α-cholinester iodide, with stirring, in ice bath, 0.4 ml 1N hydrogen chloride/acetic acid was added. After stirring in ice bath for 30 mins. and at a room temperature for 1 hr., the reaction mixture was treated as in Step Example 8 to obtain the objective compound; N-carbobenzyloxy-L-glutamic acid-α-choline ester iodide in the amount of 102 mg (yield; 91.5%).

The sample thereof resulted in single spot according to the TLC-B method to show the obtained objective compound consisting only of the α-form. NMR spectrum thereof determined according to the spectometer used in Step Example 1 was well consistant with that of the α-form.

Step Example 16 (Intermediate II→Objective Compound)

To 118 mg N-carbobenzyloxy-γ-tert.butyl-L-glutamic acid-α-cholinester paratoluenesulfonate with cooling in ice bath, 1.2 ml hydrogen chloride/chloroform (0.1% by weight) was added. The reaction mixture was treated as in Step Example 8, after stirring in ice bath for 30 mins. and at a room temperature for 5 hrs., to obtain the objective compound, N-carbobenzyloxy-L-glutamic acid-α-cholinester paratoluenesulfonate in the amount of 92 mg (yield; 86.1%).

The sample thereof resulted in single spot according to the TLC-B method to show the obtained objective compound consisting only of the α-form. NMR spectrum thereof determined according to the spectrometer used in Step Example 1 was well consistant with that of the α-form.

Step Example 17 (Intermediate→Objective Compound)

To 127 mg N-carbobenzyloxy-γ-tert.butyl-L-glutamic acid-α-cholinester paratoluenesulfonate with stirring, 0.5 ml 1N hydrogen chloride/acetic acid was added. The reaction mixture was treated as in Step Example 8, after stirring in ice bath for 30 mins., and at a room temperature for 2 hrs., to obtain the objective compound, N-carbobenzyloxy-L-glutamic acid-α-cholinester paratoluenesulfonate in the amount of 101 mg (yield; 87.8%).

The sample thereof resulted in single spot according to the TLC-B method to show the obtained objective compound consisting only of the α-form. NMR spectrum thereof determined according to the spectrometer used in Step Example 1 was well consistant with that of the α-form.

EXAMPLE

To 28.2 g N-carbobenzyloxy-γ-tert.butyl-L-glutamic acid-dicyclohexyl ammonium salt, 360 ml ethyl acetate and 49.5 ml solution of dimethylaminoethylchloride in the amount of 11.7 g, which stoichiometrically corresponds to two times the molar volume, in benzene were added to be subjected to flux in oil bath at 90° C. for 16 hrs. After cooling, precipitated dicyclohexyl ammonium chloride was filtered off and ethyl acetate phase in the filtrate was washed with diluted hydrochloride to remove excessive dimethylaminoethylchloride contained therein. The filtrate was further washed with 10% aqueous solution of hydrogen sodium bicarbonate so as to remove the unreacted starting material and then with saturated brine to be neutral, which was then treated with sulfuric sodium anhydride for dehydration to be dried and subjected to reduced pressure distillation so as to distill off ethyl acetate and obtain the Intermediate I, N-carbobenzyloxy-γ-tert.butyl-L-glutamic acid-α-dimethylaminoethyl ester in the amount of 21.5 g (yield; 96.8%).

To thus obtained N-carbobenzyloxy-γ-tert.butyl-L-glutamic acid-α-dimethylaminoethyl ester in the amount of 21.5 g, 26 ml ethyl acetate and 122 ml solution of methyl chloride of 26 g in benzene were added to stand still at a room temperature for 7 days and then to be subjected to the reduced pressure distillation to distill off the solvent and obtain the Intermediate II, N-carbobenzyloxy-γ-tert.butyl-L-glutamic acid-α-cholinester chloride in the amount of 24.0 g (yield; 99.3%).

To thus obtained N-carbobenzyloxy-γ-tert.butyl-L-glutamic acid-α-cholinester chloride in the amount of 21.5 g, with cooling in ice bath, 93 ml trifluoroacetic acid/methylene chloride (1:1 by volume) was added. After further stirring in ice bath for 30 mins. and at a room temperature for 3 hrs., the reaction mixture was subjected to the reduced pressure distillation to distill off the solvent. The residue was washed with ether to remove excessive trifluoroacetic acid and dried under vacuum to obtain N-carbobenzyloxy-L-glutamic acid-α-cholinester chloride in the amount of 20.7 g (yield; 98.3%).

The sample thereof resulted in single spot according to the TLC-B method to show the obtained product consisting only of the α-form. NMR spectrum thereof determined by the spectrometer used in Step Example 1 was as follows.

NMR $(CDCl_3+(CD_3)_2SO)\delta$: 2.02(2H, m, $—CH_2—$), 2.43(2H, m, $—CH_2CO$), 3.18(9H, s, $—N^+(CH_3)_3$), 3.77(2H, m,

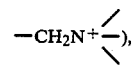

4.37(1H, m, >CHCO), 4.50(2H, m, $—OCH_2—$), 5.03(2H, s, $C_6H_5$)—$CH_2$), 7.33(5H, s, $C_6H_5—$)

From the above, it can be confirmed that the obtained product has the structure well consistent with that of N-carbobenzyloxy-L-glutanic acid-α-cholinester chloride.

What is claimed is:

1. A process for manufacturing N-carbobenzyloxy-L-glutamic acid-α-cholinester salt characterized by comprising the steps of;
    (a) that N-carbobenzyloxy-γ-tert.butyl-L-glutamic acid-dicyclohexyl-ammonium salt is reacted with dimethyl-aminoethylchloride to form N-carbobenzyloxy-γ-tert.butyl-L-glutamic acid-α-dimethylaminoethyl ester,
    (b) that obtained N-carbobenzyloxy-γ-tert.butyl-L-glutamic acid-α-dimethylaminoethyl ester is reacted with a quaternerizing agent for the dimethylamino-group to form N-carbobenzyloxy-γ-tert.butyl-L-glutamic acid-α-cholinester salt, and
    (c) that obtained N-carbobenzyloxy-γ-tert.butyl-L-glutamic acid-α-cholinester salt is subjected to mild acid treatment selectively removing of the tert.butyl-group at γ-position to obtain N-carbobenzyloxy-L-glutamic acid-α-cholinester salt.

2. The manufacturing process as claimed in claim 1, characterized in that said quaternerizing agent is any of methyl halides and organic methyl sulfonates.

3. The manufacturing process as claimed in claim 1, characterized in that said mild salt treatment is carried out with use of any selected from a class consisting of trifluoroacetic acid, hydrogen chloride, acetic acid, formic acid, propionic acid, paratoluenesulfonic acid and Lewis acids.

* * * * *